US00PP25556P3

(12) United States Plant Patent
Campo

(10) Patent No.: US PP25,556 P3
(45) Date of Patent: May 12, 2015

(54) *DRACAENA* PLANT NAMED 'CINTHO LEMON'

(50) Latin Name: *Dracaena steudneri*
Varietal Denomination: Cintho Lemon

(71) Applicant: Jan B. Campo, Bleiswijk (NL)

(72) Inventor: Jan B. Campo, Bleiswijk (NL)

(73) Assignee: Campo Participations B.V., Bleiswijk (NL)

( * ) Notice: Subject to any disclaimer, the term of this patent is extended or adjusted under 35 U.S.C. 154(b) by 81 days.

(21) Appl. No.: 13/815,471

(22) Filed: Mar. 5, 2013

(65) Prior Publication Data

US 2013/0205461 P1 Aug. 8, 2013

(51) Int. Cl.
*A01H 5/00* (2006.01)

(52) U.S. Cl.
USPC ..... Plt./383

(58) Field of Classification Search
USPC ..... Plt./383
See application file for complete search history.

(56) References Cited

PUBLICATIONS

PLUTO Plant Variety Database search for Cintho Lemon. p. 1.*

* cited by examiner

*Primary Examiner* — Annette Para
(74) *Attorney, Agent, or Firm* — C. A. Whealy

(57) ABSTRACT

A new and distinct cultivar of *Dracaena* plant named 'Cintho Lemon', characterized by its upright plant habit with foliage initially erect to outwardly arching with development; moderately vigorous growth habit; long lanceolate leaves with broad yellow green-colored centers and narrow dark green-colored boarders and longitudinal stripes; and excellent post-production longevity.

2 Drawing Sheets

Botanical designation: *Dracaena steudneri.*
Cultivar denomination: 'CINTHO LEMON'.

BACKGROUND OF THE INVENTION

The present invention relates to a new and distinct *Dracaena* plant, botanically known as *Dracaena steudneri* and hereinafter referred to by the name 'Cintho Lemon'.

The new *Dracaena* plant is a naturally-occurring whole plant mutation of the *Dracaena steudneri* 'Jelle', disclosed in U.S. Plant Pat. No. 12,677. The new *Dracaena* plant was discovered and selected by the Inventor from within a population of plants of 'Jelle' in a controlled greenhouse environment in La Guacima, Costa Rica in July, 2008.

Asexual reproduction of the new *Dracaena* plant by cuttings in La Guacima, Costa Rica since September, 2008 has shown that the unique features of this new *Dracaena* plant are stable and reproduced true to type in successive generations.

SUMMARY OF THE INVENTION

Plants of the new *Dracaena* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'Cintho Lemon'. These characteristics in combination distinguish 'Cintho Lemon' as a new and distinct *Dracaena* plant:

1. Upright plant habit with foliage initially erect to outwardly arching with development.
2. Moderately vigorous growth habit.

3. Long lanceolate leaves with broad yellow green-colored centers and narrow dark green-colored boarders and longitudinal stripes.
4. Excellent postproduction longevity.

Plants of the new *Dracaena* differ from plants of the parent, 'Jelle', primarily in leaf color as plants of 'Jelle' have leaves with narrow yellow green-colored centers and broad dark green-colored boarders.

Plants of the new *Dracaena* can be compared to plants of the *Dracaena fragrans* 'Massangeana', not patented. In side-by-side comparisons conducted in Naaldwijk, The Netherlands, plants of the new *Dracaena* differed primarily from plants of 'Massangeana' in the following characteristics:

1. Plants of the new *Dracaena* had more upright leaves than plants of 'Massangeana'.
2. Plants of the new *Dracaena* had narrower leaves than plants of 'Massangeana'.
3. Plants of the new *Dracaena* were more cold tolerant than plants of 'Massangeana'.

BRIEF DESCRIPTION OF THE PHOTOGRAPHS

The accompanying photographs illustrate the overall appearance of the new *Dracaena* plant showing the colors as true as it is reasonably possible to obtain in colored reproductions of this type. Colors in the photographs may differ slightly from the color values cited in the detailed botanical description which accurately describe the colors of the new *Dracaena* plant.

The photograph on the first sheet comprises a side perspective view of a typical plant of 'Cintho Lemon' grown in a container.

The photograph on the second sheet is a close-up view of the upper and lower leaf surfaces of a typical plant of 'Cintho Lemon'.

DETAILED BOTANICAL DESCRIPTION

The aforementioned photographs and following observations and measurements describe plants grown during the winter in 19-cm containers, with three plants per container, in a glass-covered greenhouse in Naaldwijk, The Netherlands and under cultural practices typical of commercial *Dracaena* plant production. During the production of the plants, day temperatures ranged from 18° C. to 30° C., night temperatures ranged from 18° C. to 21° C. and light levels ranged from 10 to 20 klux. Plants were six months old when the photographs and the botanical description were taken. In the following description, color references are made to The Royal Horticultural Society Colour Chart, Fifth Edition, except where general terms of ordinary dictionary significance are used.

Botanical classification: *Dracaena steudneri* 'Cintho Lemon'.

Parentage: Naturally-occurring whole plant mutation of *Dracaena steudneri* 'Jelle', disclosed in U.S. Plant Pat. No. 12,677.

Propagation:

*Type.*—By cuttings.

*Time to initiate roots, summer.*—About ten days at temperatures about 25° C.

*Time to initiate roots, winter.*—About two weeks at temperatures about 20° C.

*Time to produce a rooted young plant, summer.*—About three weeks at temperatures about 25° C.

*Time to produce a rooted young plant, winter.*—About four weeks at temperatures about 20° C.

*Root description.*—Medium in thickness, fleshy; white in color.

*Rooting habit.*—Moderately freely branching; medium density.

Plant description:

*Plant and growth habit.*—Upright plant habit with foliage initially erect to somewhat outwardly arching; inverted triangle; moderately vigorous growth habit.

*Plant height.*—About 41.1 cm.

*Plant diameter or spread.*—About 44.7 cm.

*Internode length.*—About 8 mm.

*Stem color.*—Between 144A and 145D.

*Stem strength.*—Strong.

*Stem texture.*—Smooth, glabrous.

Foliage description:

*Orientation.*—Initially erect to somewhat outwardly arching.

*Arrangement.*—Alternate, simple; sessile.

*Length.*—About 28.1 cm.

*Width.*—About 5.5 cm.

*Shape.*—Lanceolate.

*Apex.*—Acuminate.

*Margin.*—Entire; sinuate.

*Texture, upper and lower surfaces.*—Smooth, glabrous; leathery.

*Luster, upper surface.*—Moderately glossy.

*Luster, lower surface.*—Dull.

*Venation pattern.*—Parallel.

*Color.*—Developing leaves, upper surface: Center, close to N144B to N144C; longitudinal stripes and along the margins (about 6 mm in width), darker than between 137A and 147A. Developing leaves, lower surface: Center, close to 145C to 145D; longitudinal stripes and along the margins (about 6 mm in width), between 138A and 191A. Fully expanded leaves, upper surface: Center, close to slightly darker than 144A; longitudinal stripes and along the margins (about 7 mm in width), between 139A and N189A; venation, similar to lamina surface colors. Fully expanded leaves, lower surface: Center, close to 144A to 144B; longitudinal stripes and along the margins (about 7 mm in width), close to N137B; mid-vein, close to 150D, secondary venation, similar to lamina surface colors.

*Leaf sheath.*—Length: About 1.4 cm. Width: About 1 cm. Texture, upper and lower surface: Smooth, glabrous. Color, upper surface: Between 150D and 157C. Color, lower surface: Between 138A and 191A.

Flower description: Flower initiation and development has not been observed on plants of the new *Dracaena.*

Disease & pest resistance: Plants of the new *Dracaena* have not been shown to be resistant to pathogens and pests common to *Dracaena* plants.

Postproduction longevity: Excellent postproduction longevity, plants of the new *Dracaena* are durable and maintain good leaf substance indefinitely.

Temperature tolerance: Plants of the new *Dracaena* have been observed to tolerate temperatures ranging from about 5° C. to about 35° C.

It is claimed:

1. A new and distinct *Dracaena* plant named 'Cintho Lemon' as illustrated and described.

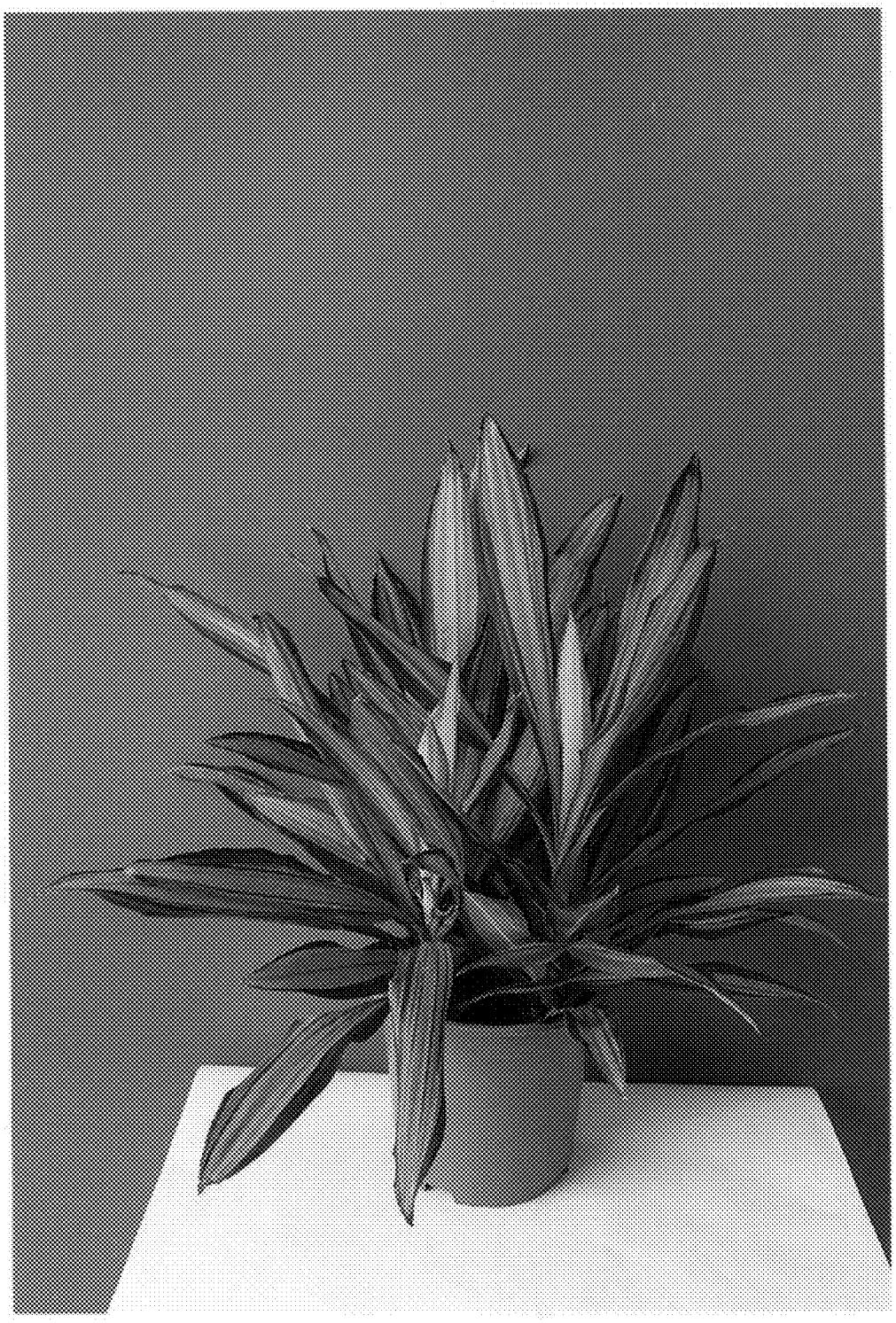

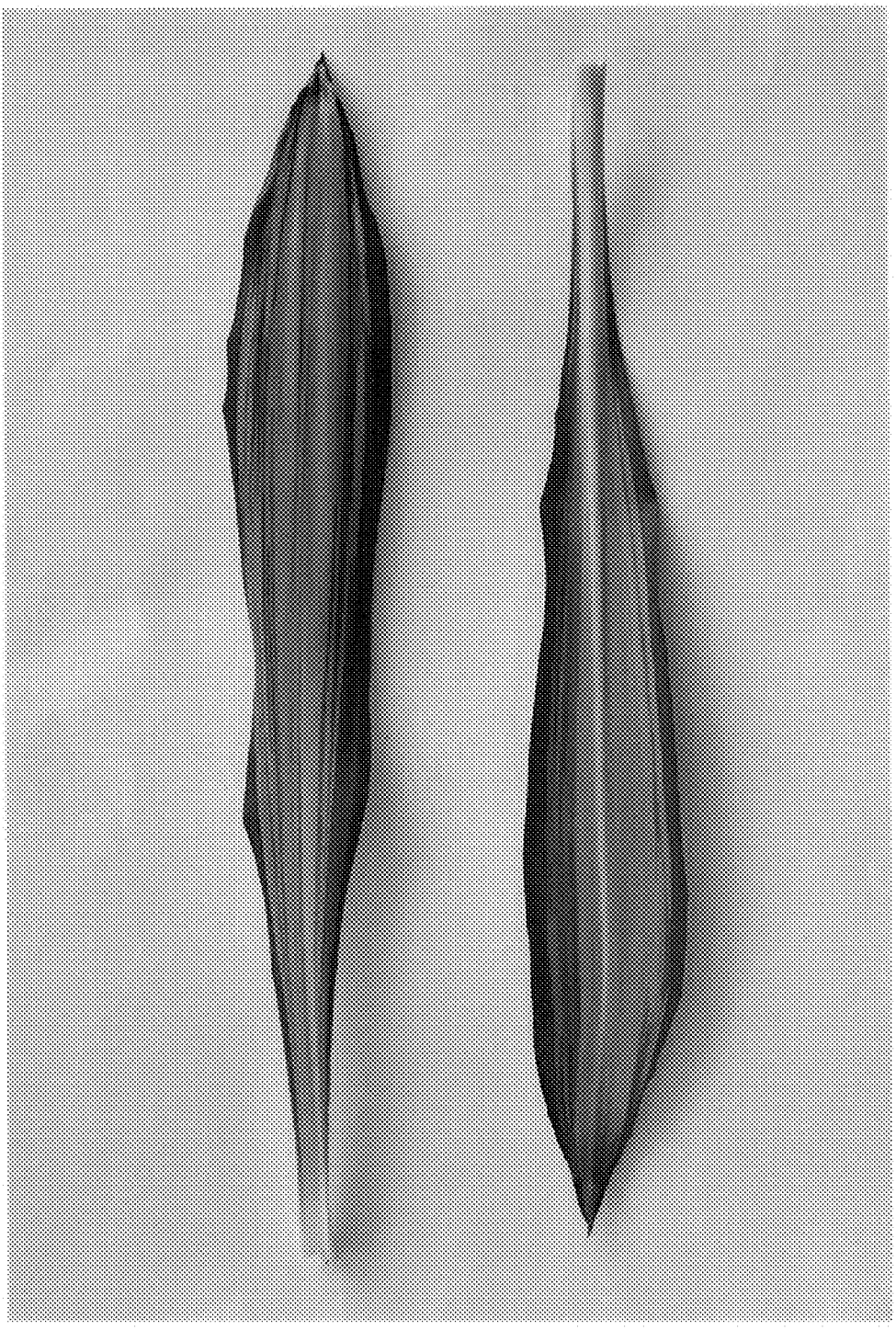

* * * * *